(12) United States Patent
Graff et al.

(10) Patent No.: US 12,163,820 B2
(45) Date of Patent: Dec. 10, 2024

(54) FILL-LEVEL MEASURING DEVICE FOR A LABORATORY CABINET DEVICE

(71) Applicant: Eppendorf SE, Hamburg (DE)

(72) Inventors: Andreas Graff, Hamburg (DE); Martin Stranzinger, Hamburg (DE)

(73) Assignee: EPPENDORF SE, Hamburg (DE)

( * ) Notice: Subject to any disclaimer, the term of this patent is extended or adjusted under 35 U.S.C. 154(b) by 965 days.

(21) Appl. No.: 16/981,264

(22) PCT Filed: Mar. 14, 2019

(86) PCT No.: PCT/EP2019/056447
§ 371 (c)(1),
(2) Date: Sep. 15, 2020

(87) PCT Pub. No.: WO2019/175325
PCT Pub. Date: Sep. 19, 2019

(65) Prior Publication Data
US 2021/0041283 A1 Feb. 11, 2021

(30) Foreign Application Priority Data
Mar. 16, 2018 (EP) .................................... 18162387

(51) Int. Cl.
*G01F 23/24* (2006.01)
*C12M 1/00* (2006.01)
*C12M 1/34* (2006.01)

(52) U.S. Cl.
CPC ........... *G01F 23/246* (2013.01); *C12M 41/14* (2013.01); *C12M 41/44* (2013.01)

(58) Field of Classification Search
CPC ...... G01F 23/246; C12M 41/14; C12M 41/44
See application file for complete search history.

(56) References Cited

FOREIGN PATENT DOCUMENTS

| EP | 2067849 A1 | * | 6/2009 | ............ C12M 37/00 |
|----|----|----|----|----|
| JP | H3-233325 A | | 10/1991 | |
| JP | H7-260547 A | | 10/1995 | |
| JP | 2001-159556 A | | 6/2001 | |
| JP | 2002188977 A | * | 7/2002 | |
| WO | WO 2018/037482 A1 | | 3/2018 | |

OTHER PUBLICATIONS

English Machine Translation of Endo, JP-2002188977-A, Jul. 2002 (Year: 2002).*

* cited by examiner

*Primary Examiner* — David Z Huang
(74) *Attorney, Agent, or Firm* — Todd Lorenz

(57) ABSTRACT

The invention relates to a fill-level measuring device for a laboratory cabinet device, for measuring a fill-level in a liquid container in the interior of the laboratory cabinet device, which detects the fill-level by comparing the measurement of two NTC temperature sensors, the first of which is arranged in the air of the interior and the second in the liquid of the liquid container.

16 Claims, 5 Drawing Sheets

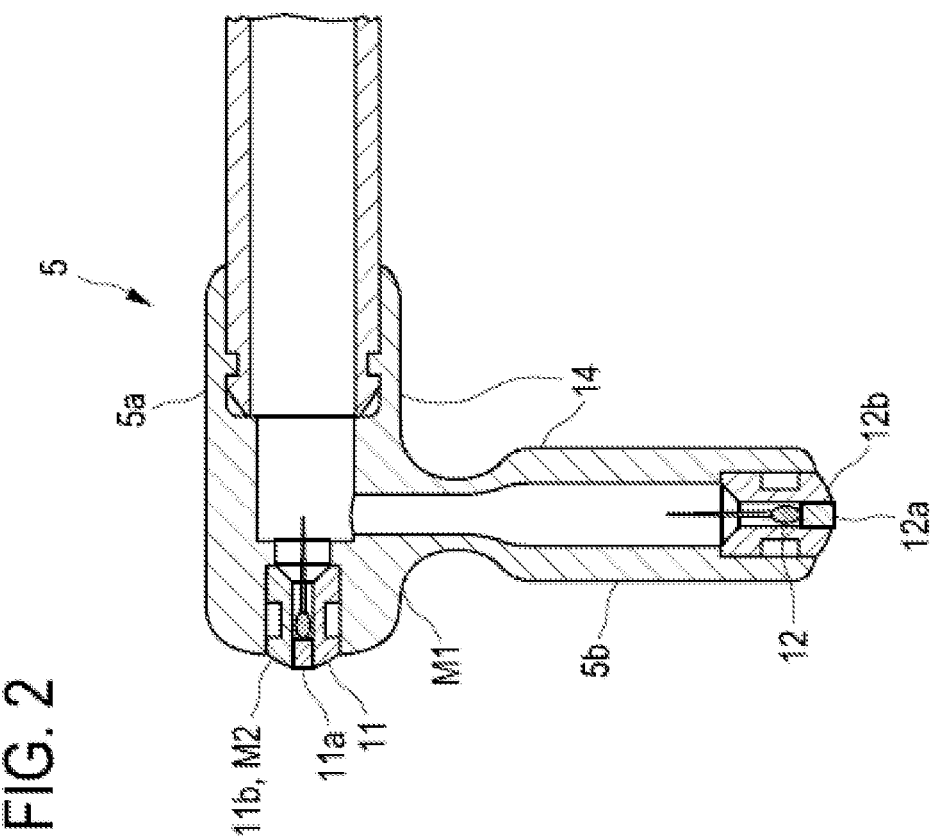

FILL-LEVEL MEASURING DEVICE FOR A LABORATORY CABINET DEVICE

The invention relates to a fill-level measuring device for a laboratory cabinet device, for measuring a fill-level in a liquid container in the interior of the laboratory cabinet device. The laboratory cabinet device serves for the storage of laboratory samples and is in particular a tempering cabinet for the tempering of laboratory samples, especially an incubator for the growth of cell cultures.

Such incubators are used in biological and medical laboratories to keep cells in cell cultures under controlled environmental conditions, thus enabling the growth of living cells in vitro. For this purpose, the temperature and the gas composition or the humidity of the atmosphere inside an incubator chamber isolated from the environment, are kept at the desired values by the devices of the incubator. Eukaryotic cells require CO2 incubators. The atmosphere is formed by air having a certain CO2 and 02 content and a certain humidity, a suitable temperature is often 37° C. Such temperature control cabinets comprise a housing, for example an outer housing, with a housing opening through which the user stores and removes the samples inside the housing. Thereby, water vapor regularly escapes from the interior. The incubators therefore contain an upwardly open liquid container filled with water, by means of which a relative humidity of more than 90% is produced in the interior by evaporation of the water. In order to record water consumption and prevent the water tank from being completely emptied, such temperature control cabinets often have fill-level measuring devices.

An incubator with two NTC sensors is known from EP 2 067 849 B1, both of which are arranged in the incubator's water bath at one measurement level, wherein the NTC sensors are operated at different temperatures and their output voltages are evaluated to detect when the temperature falls below the measurement level.

It is an object of the present invention to provide a reliable and efficiently designed fill-level measuring device for a laboratory cabinet device, in particular a temperature control cabinet.

The invention solves this problem by the fill-level measuring device according to claim 1. Preferred embodiments are in particular subject of the dependent claims.

The fill-level measuring device according to the invention comprises NTC (negative temperature coefficient) temperature sensors, also known as NTC thermistors. Such temperature sensors are self-regulating. They are supplied with a current, which is as large that self-heating occurs. The current thus initially heats them up and keeps them at an excess temperature above the temperature of their surroundings. Due to the NTC behavior, according to which the electrical resistance increases with the decreasing temperature—caused by the heat emission to the environment—the power is self-limiting and a stationary state of equilibrium is established. The first NTC temperature sensor is positioned, such that it never comes into contact with the liquid, the second NTC temperature sensor is normally in the liquid and changes its heat output as soon as the liquid level drops below the second NTC temperature sensor. The first NTC temperature sensor therefore serves as a reference sensor, which fulfils its reference function independently of the temperature of the interior of the laboratory cabinet device, thereby ensuring particularly reliable operation of the fill-level measuring device, which is implemented with simple means.

The first NTC temperature sensor and the second NTC temperature sensor emit a different thermal output to their respective environment if these environments have different thermal conductivities. Since the thermal conductivity of air is much worse than that of a liquid, especially of water, the second NTC temperature sensor emits a higher thermal output than the first NTC temperature sensor. This results in a higher electrical resistance at the second NTC temperature sensor than at the first NTC temperature sensor, such that the voltage across the second NTC temperature sensor drops more than at the first NTC temperature sensor as long as the second NTC temperature sensor contacts the liquid. If the second NTC temperature sensor is then exposed to the same environment (e.g. air) as the first NTC temperature sensor when the fill-level drops, the resistance of the second NTC temperature sensor changes or adjusts to the resistance of the first NTC temperature sensor, and this change can be measured. In particular, the magnitude of the difference between the output voltages of the first and second NTC temperature sensors in the first state is greater, when the second NTC temperature sensor is exposed to liquid at normal fill-level and the first to air than in the second state when both NTC temperature sensors are exposed to air.

The first and second NTC temperature sensors are preferably selected to operate at a low voltage of preferably 15 to 35 volts, preferably 20 to 30 volts. Therefore, low-impedance NTC temperature sensors with 1-2 kOhm are preferably used. They are preferably selected to tolerate ambient temperatures of up to 200° C., preferably up to 190° C. and preferably up to 180° C. in normal operation or to withstand these temperatures without damage. This allows such temperature sensors to remain in the interior of a laboratory cabinet, in particular a temperature control cabinet or incubator, when heated to the high temperature mentioned, for example for the purpose of sterilizing the interior at 180° C. The use of the laboratory cabinet device equipped with such a fill-level measuring device is therefore particularly efficient, because the fill-level measuring device does not have to be removed before sterilization. A suitable NTC temperature sensor is for example the G2K3348 Radial Glass Thermistor from Measurement Specialties, Hampton, Virginia, USA.

The electronic measuring device preferably comprises electronic circuits. The electronic measuring device is preferably configured to determine a first comparison value when—or as long as—the fill-level in the liquid container is above the position of the second NTC temperature sensor, and to detect a second comparison value deviating from the first comparison value, when the fill-level in the liquid container has fallen below the position of the second NTC temperature sensor. The first and second comparison value are determined in particular by continuously recording the comparison value, in particular a difference value, of the first and second electrical quantity and then comparing it with a reference value in order to decide, whether a first comparison value is present (first state or normal state) or a second comparison value is present (second state or fault state).

Preferably, the fill-level measuring device comprises an evaluation device which is, in particular, a programmable microcontroller or computer for carrying out the evaluation in question. The evaluation device in particular also comprises an A/D converter (AD converter, ADC) for digitising analogue measurement signals from the electronic measuring device. The evaluation device may be part of an electronic control unit, which controls the electrically controllable functions, in particular the regulation of the interior temperature of the laboratory cabinet device. The evaluation device preferably has a data storage device for the volatile or non-volatile storage of data, and/or preferably a data processing device, which is set up in particular to distinguish the second comparison value from the first comparison value by comparing the continuously measured comparison value with a reference value, which is stored in the data storage device. The data storage device and/or the data processing device can be components of an electronic control device, which controls the electrically controllable functions, in particular the regulation of the interior temperature of the laboratory cabinet device.

Preferably the electronic measuring device and/or the evaluation device is configured to generate an output signal and/or output data depending on the evaluation of the comparison value, which is output to the user via a user interface device. In this way, the user can be informed, in particular if the filling level drops below a threshold value. This threshold corresponds to the mentioned reference value. The user interface device may, in particular, provide the information on whether the fill-level falls below a threshold value on a display of the fill-level measurement device, or of the laboratory cabinet device comprising this fill-level measurement device. The user interface device can also be configured to emit an audible warning signal and/or send output data via a remote data link, for example via a LAN, to which the laboratory cabinet device is connected, when the fill-level falls below a threshold value.

The electronic measuring device preferably comprises an electronic circuit, which includes the first NTC temperature sensor and the second NTC temperature sensor. In particular, the first and second electrical quantities are evaluated in analog-electrical form. However, it is also possible that the first and second electrical quantities are digitized and then digitally evaluated. Preferably, at least one A/D converter is provided, which digitizes the first and the second electrical quantity.

Preferably, the electronic measuring device is configured in such a way that the first and the second electrical quantity are analog-electrically and/or evaluated by forming a difference between the first and the second electrical quantity, analog or digital, and the comparison value is based on the difference between the first and the second electrical quantity or, the comparison value includes the difference value of the first and second electrical quantity, the comparison value thus being in particular the difference between the first and second electrical quantity or the difference between the second and first electrical quantity. Instead of, or in addition to, difference formation, the comparison of the first and second electrical quantities may also involve another mathematical operation, in particular addition, multiplication and, in particular, quotient formation of the first and second electrical quantities.

The electronic measuring device is preferably configured such that the first and second NTC temperature sensors are arranged in a bridge circuit. A bridge circuit is in particular a Wheatstone bridge. Such a circuit is particularly suitable for the precise evaluation of small resistance changes or small voltage changes. The electronic measuring device is preferably configured such that the bridge voltage of the bridge circuit is used as the first and second comparison value.

The electronic measuring device preferably comprises a voltage-controlled current source as electronic circuit, whose input voltage is the bridge voltage. The output current is preferably used to generate a ground-referenced output voltage via a load resistor, which in particular routes to an ADC input.

The fill-level measuring device preferably comprises a holding device for holding the first and/or the second NTC temperature sensor at a distance from an inner wall of the laboratory cabinet device. The first and/or the second NTC temperature sensor are preferably held by the holding device in such a way that in the normal case, when the liquid container is sufficiently filled with liquid, the first NTC temperature sensor is arranged outside the liquid and in the normal case the second NTC temperature sensor is arranged inside the liquid, and in the fault case, when the liquid container is not sufficiently filled with liquid, the first NTC temperature sensor is still arranged outside the liquid and in the fault case the second NTC temperature sensor is also arranged outside the liquid.

Preferably, the holding device is an integral part or a part made of interconnected components and/or in particular comprises a single holding arm connected to the laboratory cabinet device. Thereby, the holding device is easy to install, compact and easier to clean and to maintain. However, the support may also comprise several separate components, in particular several support arms connected to the laboratory cabinet, if necessary.

Preferably, the holding device comprises a holding arm which can be attached to an inner wall, in particular inner rear wall, of the laboratory cabinet device, which is provided, in particular for a horizontally directed arrangement and which carries the first NTC temperature sensor and to which preferably a, in particular, elastically deformable second holding arm is attached, which is provided, in particular, for a vertically downwardly directed arrangement and which carries the second NTC temperature sensor. An elastically deformable second support arm with an attached second NTC temperature sensor offers the advantage that this support arm can be bent and the second NTC temperature sensor can therefore be lifted without having to remove the support arm. Therefore, removing the liquid container, especially the tub, is facilitated when the second NTC temperature sensor is mounted.

Preferably, the holding device has an encapsulation device made of a first material (M1) for partial or—essentially—complete encapsulation of the first and/or the second NTC temperature sensor. Preferably, the first NTC temperature sensor has at least one—or exactly one—sensor contact surface which is thermally coupled to the temperature-dependent resistance of the NTC temperature sensor and which is directed outwards where it borders on the environment of the NTC temperature sensor. The NTC temperature sensor and its sensor contact surface are preferably enclosed by a socket, and, in particular, largely encapsulated by the capsule device. The second NTC temperature sensor also preferably comprises a sensor contact surface, which is called the second sensor contact surface. The at least one sensor contact surface of the first and/or the second NTC temperature sensor is made of a second material M2. The capsule device preferably encloses the at least one sensor contact surface. Preferably, the capsule device and the at least one sensor contact surface limit the first and/or the second NTC temperature sensor to the outside. In particular, the second material (M2) has a higher thermal conductivity than the first material (M1).

With a temperature control cabinet, especially a CO2 incubator, the requirement is that the precisely defined temperature of the interior should not be influenced. However, the NTC temperature sensors are operated at an excess temperature. Because the capsule device is made of poorly heat-conducting material M1 the sensors are thermally insulated from the outside. On the one hand, this prevents a disturbing heating of the interior and, on the other hand, this prevents an unwanted cooling of the NTC temperature sensors. The heat flow between sensor and interior concentrates especially on the small area of the at least one sensor contact surface. This embodiment allows low-power NTC temperature sensors to be used.

The first material (M1) is preferably a plastic, in particular a rubber or elastomer, which is particularly resistant to temperatures of up to 200° C. or 180° C. The second material (M2) is preferably a metal, in particular, stainless steel.

Preferably, the first and/or second NTC temperature sensor each have a socket made of a material M3, which is also less thermally conductive than the material M2 and further insulates the sensor thermally. Preferably the first NTC temperature sensor and its sensor contact surface and/or the second NTC temperature sensor and its sensor contact surface are each enclosed by a socket, so that preferably the capsule device, the socket of the first and/or of the second NTC temperature sensor and the at least one sensor contact surface limit the first and/or the second NTC temperature sensor outwards to the interior of the laboratory cabinet device. Preferably the third material (M3) is polyether ether ketone (PEEK), which provides excellent thermal and chemical resistance.

Preferably, the holding device, the first NTC temperature sensor and the second NTC temperature sensor are made of materials that can withstand operating temperatures of the interior of the laboratory cabinet device of up to 180° C. or up to 200° C. without damage.

The invention also relates in particular to a laboratory cabinet device for storing laboratory samples, in particular a temperature control cabinet, in particular an incubator, with a liquid container in the interior of the laboratory cabinet device and a fill-level measuring device according to the invention for measuring a fill-level in the liquid container. The fill-level measuring device is used in particular to measure the fill-level of the liquid container of an air humidifier of an incubator.

The laboratory cabinet device for storing laboratory samples is, in particular, a tempering cabinet for tempering laboratory samples. Such devices are electrically operated and have a voltage connection. The NTC temperature sensors can also be operated via this connection.

The temperature control cabinet controls the temperature of the laboratory samples, i.e. it keeps the inside of the housing—and thus the laboratory samples stored there—at a target temperature within tolerances, it, in particular, keeps the inside of the housing at a setpoint temperature that can be set by the user. This can be above room temperature (ambient temperature), as it is the case with a warming cabinet or incubator, or below room temperature, as it is the case with a refrigerator or freezer. In the case of a laboratory cabinet designed as a climatic cabinet, a climatic parameter, which characterizes the inside of the cabinet, is preferably also controlled within tolerances. This climate parameter can be the humidity of the air and/or a gas concentration, e.g. a $CO_2$, $N_2$ and/or $O_2$ concentration. Such a climate chamber is for example a $CO_2$ incubator for laboratory samples consisting of living cell cultures. Temperature cabinets or $CO_2$ incubators are used in biological and medical laboratories to keep cells in cell culture under controlled environmental conditions, thus enabling the growth of living cells in vitro.

For this purpose, the temperature and the gas composition or the humidity of the atmosphere inside an incubator chamber isolated from the environment are kept at the desired values by the apparatus of the incubator. Eukaryotic cells require $CO_2$ incubators. The atmosphere is formed by air with a certain $CO_2$ and $O_2$ content and a certain relative humidity of over 90%, especially 95%, whereas a suitable temperature is often 37° C., but this content can be set by the user according to the requirements of the laboratory samples.

The housing of the laboratory cabinet device is preferably an external housing whose housing walls are in contact with the environment. However, the housing can also be an inner housing located inside an outer housing. For example, an incubator may have at least one chamber serving as an inner housing, which can be closed by at least one housing door or chamber door. In the closed position, the housing door closes the inside of the housing preferably gas-tight, which is achieved, in particular, by at least one sealing device of the housing door or of the frame of the housing opening. However, the invention also concerns laboratory cabinet devices with a housing, which does not completely seal the inside of the housing from the environment.

The laboratory cabinet device preferably contains a holding device for holding the first and/or the second NTC temperature sensor at a distance from an inner wall and from a bottom wall of the laboratory cabinet device, in particular at a distance from an inner wall and from a bottom wall of a housing or a chamber of the laboratory cabinet device. In particular, a normal operating condition of the laboratory cabinet device is provided, also known as the "first condition", during which the first NTC temperature sensor is located outside the liquid of the liquid container of the laboratory cabinet device and the second NTC temperature sensor is located inside the liquid of the liquid container. In particular, a fault operating condition of the laboratory cabinet device is provided, also referred to as the "second condition", during which the first NTC temperature sensor is located outside the liquid of the liquid container of the laboratory cabinet device and the second NTC temperature sensor is located outside the liquid of the liquid container. The laboratory cabinet device and/or its control device and/or its measuring device are configured to distinguish the fault operating condition from the normal operating condition by measuring the reference value and, in particular, to provide the user with information on the occurrence of the fault operating condition via a user interface device.

Further preferred embodiments of the laboratory cabinet device according to the invention can be found in the description of the embodiments according to the figures.

It shows:

FIG. 2 shows a holding device for holding the first and second NTC temperature sensor of an exemplary fill-level measuring device according to the invention, which can be used especially in the laboratory cabinet according to FIGS. 1a, 1b.

Figure 1A:
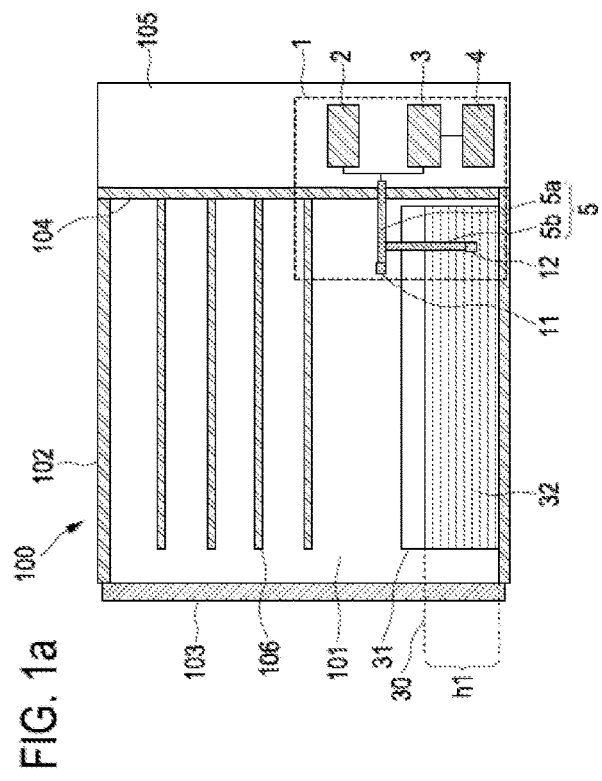
FIG. 1a shows a schematic side view of a laboratory cabinet device provided with an exemplary fill-level measuring device according to the invention, in a first state, in which the second NTC temperature sensor is placed inside the liquid of the liquid container of the laboratory cabinet device.
Figure 1B:
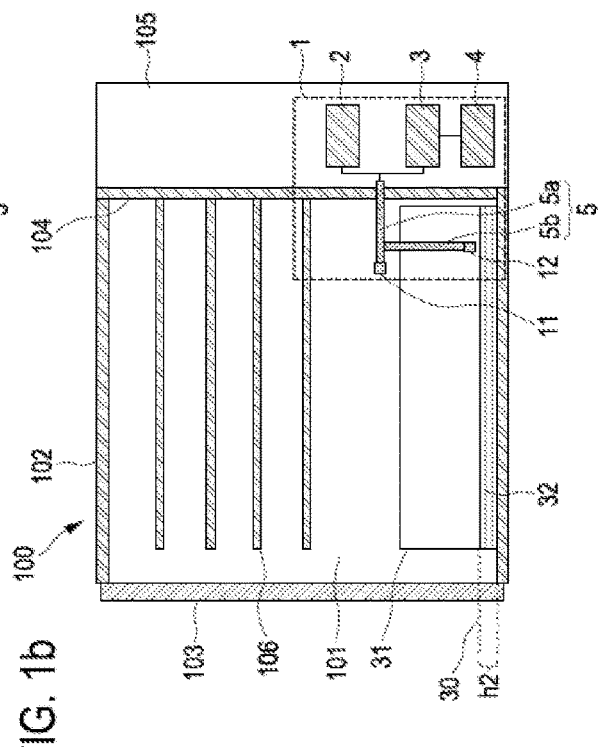
FIG. 1b shows a schematic side view of a laboratory cabinet device provided with an exemplary fill-level measuring device according to the invention, in a second state, in which the second NTC temperature sensor is no longer located within the liquid of the liquid container of the laboratory cabinet device.

FIG. 1a shows a laboratory cabinet device 100 provided with a fill-level measuring device 1 in a first state, in which the second NTC temperature sensor 12 is placed inside the liquid 32 of the liquid container 31 of the laboratory cabinet device 100. FIG. 1b shows the same laboratory cabinet device 100 in a second state, in which the second NTC temperature sensor 12 is no longer located inside the liquid 32 of the liquid container 31 of the laboratory cabinet device, for example, due to evaporation of the liquid, especially water.

The present laboratory cabinet device 100 is a CO2 incubator for the growth of living cell cultures. The Incubator 100 is shown in simplified form. It comprises a housing 102, which thermally isolates the inner chamber 101, which is temperature-controlled (=tempered) to 37° C., from the environment. The housing opening is closed by a housing door 103 and allows access to the interior 101. In the interior there are perforated shelves 106, at the bottom of the interior there is the liquid container 31 designed as a water tub, in which the liquid is arranged horizontally, following gravity, and parallel to the base plate of the housing. The rear wall 104 of the housing is perpendicular to the base plate and thus vertically arranged. On the inside of this rear wall, the holding device 5 of the incubator is mounted in the interior 101 of the incubator.

Holding device 5 of the incubator comprises a horizontally arranged first holding arm 5a, which is attached to the rear wall 104. The second support arm 5b is attached to the vertically downward pointing side of the first support arm 5a. The first NTC temperature sensor 11 is attached to the end of the first support arm 5a, the second NTC temperature sensor 12 is attached to the end of the second support arm 5b. Due to this arrangement the first NTC temperature sensor 11 is always above the liquid surface 30 and thus always outside the liquid. The first NTC temperature sensor 11 basically always borders on the gaseous atmosphere (air with controlled CO2, H2O composition) of the interior 101. The second NTC temperature sensor 12 always reaches into the liquid in the first state of a sufficiently filled water container 31, as shown in FIG. 1a. In the (fault) case or in the second state of an insufficiently filled water container 31, as shown in FIG. 1b, the second NTC temperature sensor 12 is no longer in contact with the liquid of the liquid surface 30. In the first state the fill-level, measured from the bottom of the water container 31, has the height h1. In the second state the fill-level, measured from the bottom of the water tank 31, has the height h2.

The fill-level measuring device is framed in FIGS. 1a and 1b with a dotted rectangle with the reference sign 1. The first holding arm 5a projects through a port in the rear wall 104 of the housing into the control chamber 105 of the incubator, where the power supply 2, the electronic measuring device 3 and the evaluation device 4 are located.

The fill-level measuring device 1 is used to measure the fill-level 30 in the liquid container 31 and comprises: a first NTC temperature sensor 11, which can be or is arranged outside the liquid 32 of the liquid container 31, a second NTC temperature sensor 12, which can be or is normally arranged inside the liquid 32 of the liquid container 31. The level measuring device 1 comprises a power supply device 2 from which the first NTC temperature sensor 11 and the second NTC temperature sensor 12 are supplied with power in such a way that the first NTC temperature sensor 11 and the second NTC temperature sensor 12 each have an excess temperature T_NTC, which is greater than the temperature T_inside in the interior 101 of the laboratory cabinet device. For example, if T_inside=37° C., then T_NTC is preferably 4 to 15° C. higher, especially between 40 and 50° C.

Figure 3:
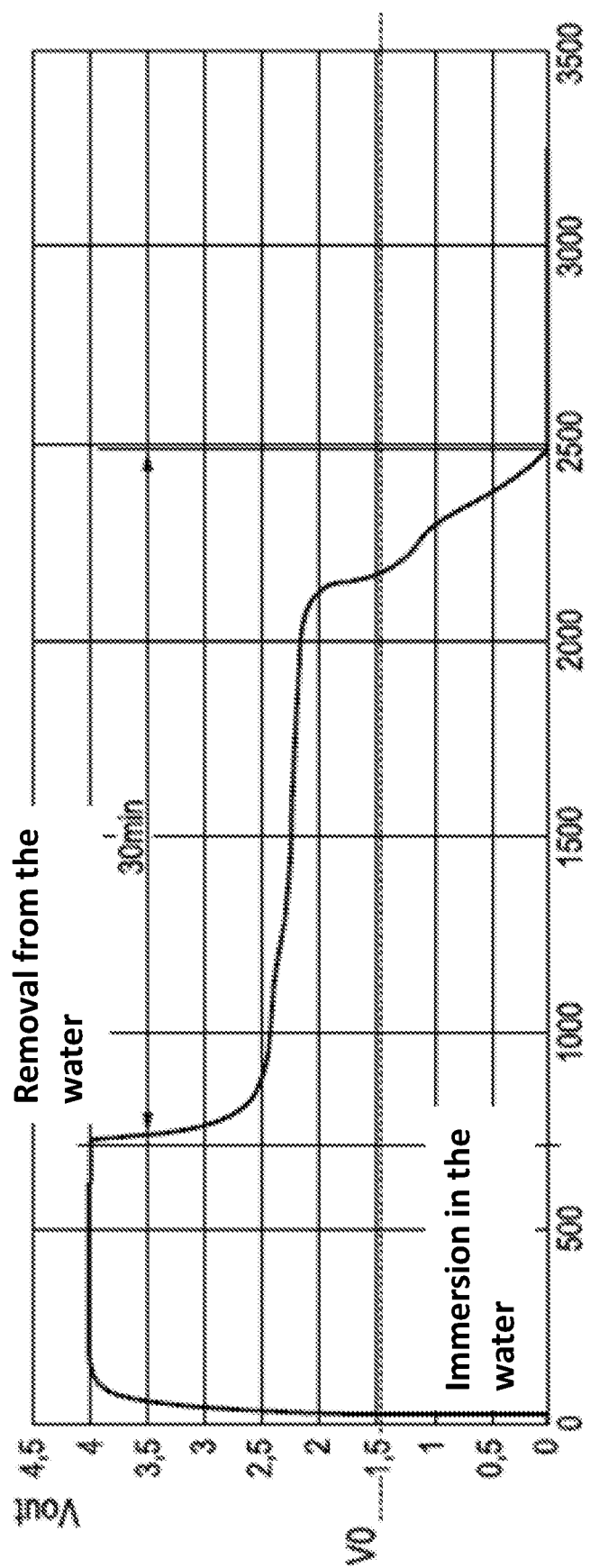
FIG. 3 shows the diagram of a comparison value "Vout", which was continuously determined by the electronic measuring device of an exemplary fill-level measuring device according to the invention, while at a certain point in time (after 750 s) the second NTC temperature sensor was removed from the liquid.
Figure 5:
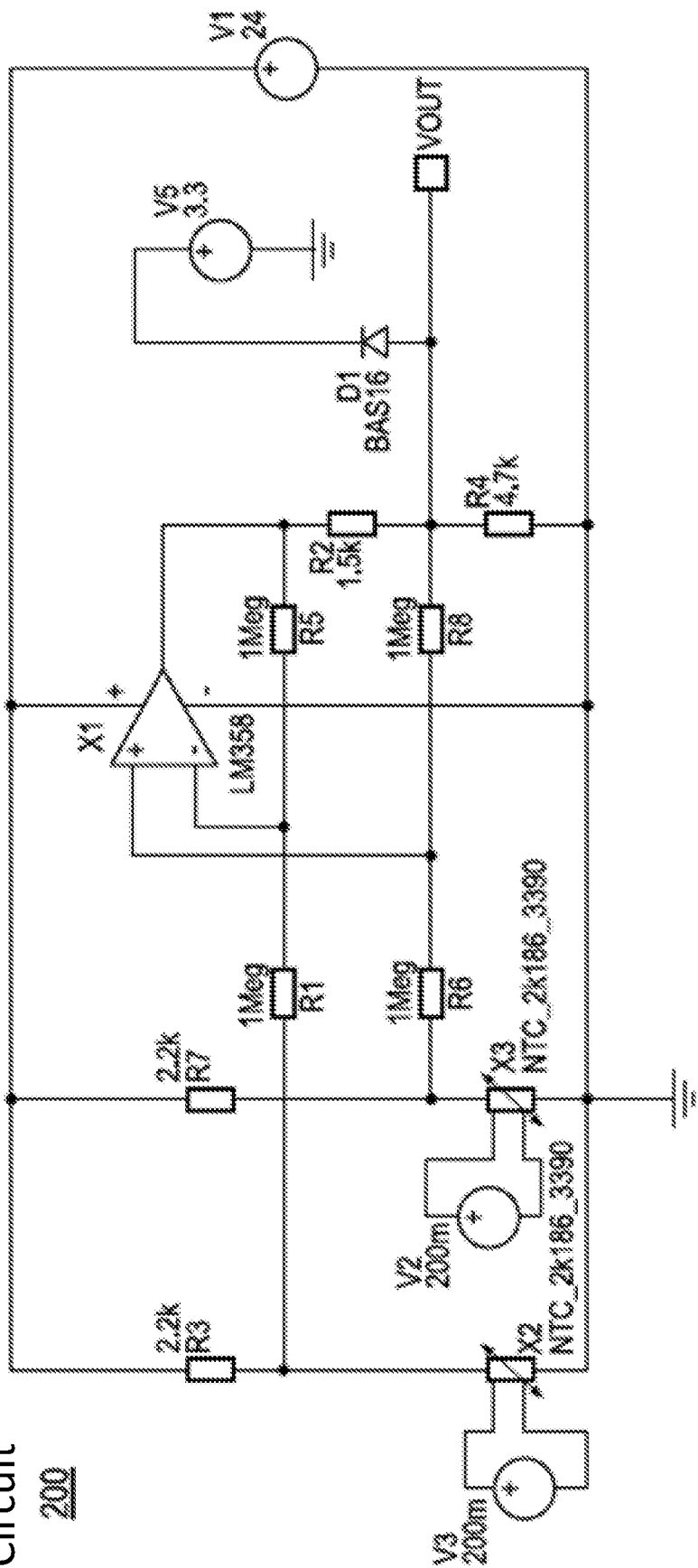
FIG. 5 shows the circuit diagram of the circuit of the electronic measuring device of an exemplary fill-level measuring device according to the invention, which is used in particular in the fill-level measuring device of FIGS. 1a, 1b.

The electronic measuring device 3 is configured to detect a first electrical quantity of the first NTC temperature sensor 11 influenced by the temperature of the first NTC temperature sensor 11, e.g. a voltage change at the first NTC temperature sensor, and a second electrical quantity of the second NTC temperature sensor 12 influenced by the temperature of the second NTC temperature sensor 12, e.g. a voltage change at the second NTC temperature sensor, and to determine a comparison value, e.g. "Vout" in FIGS. 3 and 5, by continuous comparison of the first and second electrical quantities, i.e. a comparison carried out at short time intervals between e.g. 50 ms and 1 min.

The evaluation device 4 comprises a data storage device and a data processing device (respectively not shown), which is configured to distinguish the second comparison value from the first comparison value by comparing the continuously measured comparison value with a reference value, which is stored in the data storage device.

The electronic measuring device 3 is configured to determine a first comparison value when the fill-level 30 in the liquid container is above the second NTC temperature sensor 12, as shown in FIG. 1a, and to detect a second comparison value deviating from the first comparison value when the fill-level 30 in the liquid container has fallen below the second NTC temperature sensor 12. The first comparison value Vout in FIG. 3 at time t=0 is approximately Vout=4V, the second comparison value Vout at time t=2500 s is Vout=0V. The evaluation device 4 uses a reference value V0 stored in the data storage device of the evaluation device 4, to decide whether the minimum permissible filling level of the liquid container has been undercut. The value V0 is a threshold value and is present at approximately V0=1.5V, which is reached here at the time t=2200 s. In the diagram in FIG. 3 this is approximately 1450 s after the second NTC temperature sensor 12 has been removed for test purposes from the water bath 32 in which it was placed at the time t=0.

From FIG. 3 it appears that the second NTC temperature sensor 12 requires a time of approximately 120 s after insertion into the water until a steady-state equilibrium of the temperature of the NTC sensor is reached, which results from the power provided to the sensor as a current supply and the heat dissipation via its sensor contact surface. The course of the curve between t=750 s and t=2500 s results from the fact that the sensor contact surface is still wetted by a meniscus of liquid 32 for a while, before the liquid is no longer in contact with the sensor contact surface and the differential measurement between the first and second NTC temperature sensor results in a reference voltage of 0V.

The evaluation device 4 comprises a data storage device and a data processing device, which respectively are not shown here, which are configured to distinguish the second comparison value from the first comparison value by comparing the continuously measured comparison value with a reference value, which is stored in the data storage device.

The electronic measuring device 3 is set up such that the first and second NTC temperature sensors are arranged in a bridge circuit 200, see FIG. 5. As the first and the second comparison value, the bridge voltage Vout of the bridge circuit 200 is respectively used.

Figure 4:
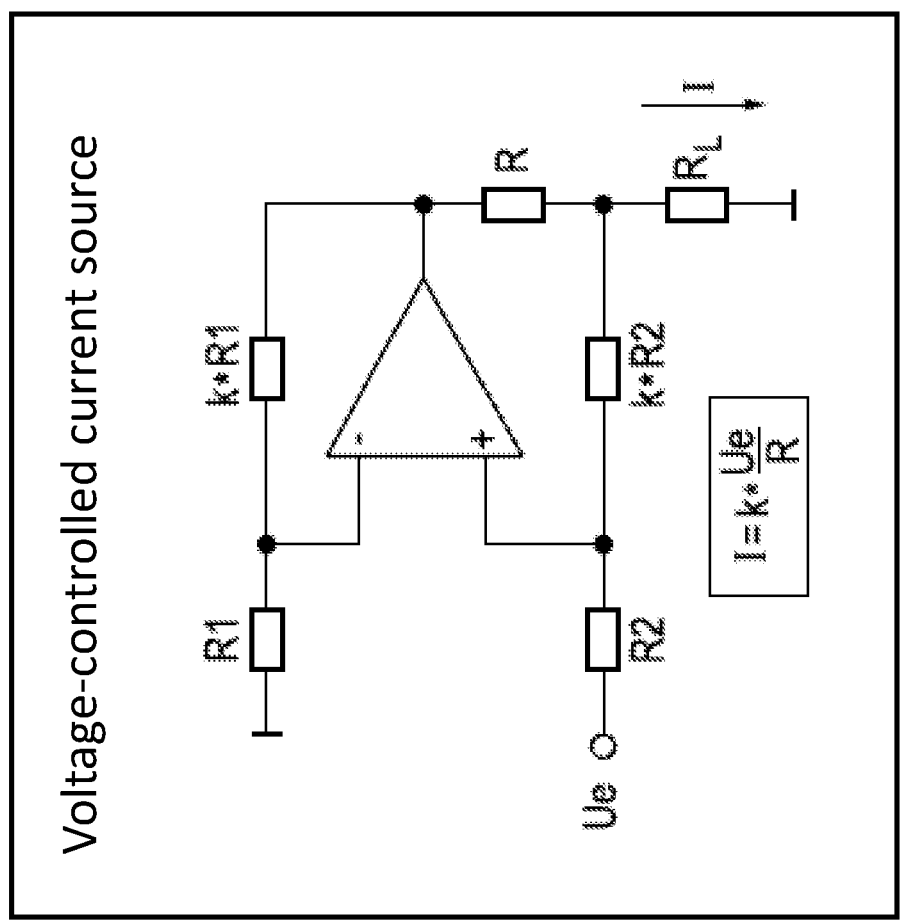
FIG. 4 shows the circuit principle of a voltage-controlled current source, which is used in the electronic measuring device of an exemplary fill-level measuring device according to the invention, in particular in the circuit of FIG. 5.

The electronic measuring device 3 comprises a voltage-controlled current source as electronic circuit 400 (see FIG. 4), whose input voltage is the bridge voltage. The output current is used to generate a ground-referenced output voltage via a load resistor, which goes to an ADC input.

In FIG. 5 the first NTC temperature sensor is marked "X2, NTC_2k186_3390", the second NTC temperature sensor is marked "X3, NTC_2k186_3390". The input voltage is the bridge voltage of the NTC temperature sensors (differential measurement). The output current of the operational amplifier is used to generate a ground-referenced output voltage via R4, which routes to an ADC input. The sensitivity (gain) of the circuit is set by use of R2. D1 limits the ADC input voltage. The following applies:

$$V\text{out}=R4*(U\_NTC\_x3-U\_NTC\_x2)/R2$$

R3/R7 set the measuring current of the NTC's such that there is a considerable heating.

The fill-level measuring device comprises the holding device 5 for holding the first and/or the second NTC temperature sensor at a distance from the inner wall 104 of the laboratory cabinet device, which is explained using FIG. 2. The holding device 5 comprises a holding arm 5a, which can be attached to an inner wall of the laboratory cabinet device 100 and which carries the first NTC temperature sensor 11 and to which a more elastically deformable second holding arm 5b is attached, which is provided for the vertically downward arrangement and which carries the second NTC temperature sensor 12. The holding device 5 comprises a capsule device 14 made of a first material M1 and at least one sensor contact surface 11a, 12a of the first and/or the second NTC temperature sensor 11, 12 made of a second material M2, such that the capsule device 14 encloses the two sensor contact surfaces 11a, 12a. The capsule device 14 and the two sensor contact surfaces 11a, 12a limit the first and the second NTC temperature sensor 11, 12 to the outside. The second material M2 has a higher thermal conductivity than the first material M1. The first material M1 is a plastic, especially rubber or an elastomer, and the second material M2 is stainless steel in the herewith case. In this way, the technical problem of selecting the NTC temperature sensors and of selecting the mechanical design of the capsule device 14 of the NTC temperature sensors was solved. Since the NTC temperature sensor transfers the thermal energy to the capsule device, the NTC temperature sensor must be large enough and the capsule device must be designed in such a way that the NTC temperature sensor heats up significantly to the excess temperature T_NTC, here approx. 50° C. Low-resistance types (R25 approx. 1k–2k) are particularly suitable for the probes, because otherwise the preferred supply voltage (24V) is not sufficient to provide the necessary current. Since the NTC temperature sensors should be suitable for 180° C., glass passivated types are preferred.

The first NTC temperature sensor 11 and its sensor contact surface 11a and the second NTC temperature sensor 12 and its sensor contact surface 12a are each enclosed by a cylinder-like socket 11b, 12b so that the capsule device 14, the socket 11b, 12b of the first and second NTC temperature sensors 11, 12 and the at least one sensor contact surface 11a, 12a outwardly delimit the first and second NTC temperature sensors 11, 12. The socket 11b, 12b consists of a third material M3, here polyetheretherketone (PEEK), and is therefore temperature resistant and chemically inert. The holding device 5, the first NTC temperature sensor 11 and the second NTC temperature sensor 12 consist of materials that can withstand operating temperatures of the interior of the laboratory cabinet device of up to 180° C.

The invention claimed is:

1. Fill-level measuring device (1) for measuring a fill-level (30) in a liquid container (31) in the interior (101) of a laboratory cabinet device (100), comprising
a first NTC (negative temperature coefficient) temperature sensor (11) arrangeable outside the liquid (32) of the liquid container (31),
a second NTC temperature sensor (12) arrangeable within the liquid (32) of the liquid container (31)
a power supply device (2) from which the first NTC temperature sensor (11) and the second NTC temperature sensor (12) are supplied with power such that the first NTC temperature sensor (11) and the second NTC temperature sensor (12) each have an excess temperature (T_NTC) which is greater than the temperature (T_inside) in the interior (101) of the laboratory cabinet device, and
an electronic measuring device (3) arranged to detect a first electrical quantity of the first NTC temperature sensor (11) influenced by the temperature of the first NTC temperature sensor (11) and to detect a second electrical quantity of the second NTC temperature sensor (12) influenced by the temperature of the second NTC temperature sensor (12), and to determine a comparison value by continuous comparison of the first and second electrical quantity,
characterized in that
a holding device (5) for holding the first and the second NTC temperature sensor at a distance from an inner wall and a bottom wall of the laboratory cabinet device (100), the holding device (5) having a holding arm (5a), which can be fastened to the inner wall of the laboratory cabinet device (100) and which carries the first NTC temperature sensor (11) and to which an elastically deformable second holding arm (5b) is attached, which is provided for a vertically downwardly directed arrangement and which carries the second NTC temperature sensor (12).

2. Fill-level measuring device according to claim 1, characterized in that the electronic measuring device is set up to determine a first comparison value when the fill-level (30) in the liquid container is above the second NTC temperature sensor (12), and to detect a second comparison value differing from the first comparison value when the fill-level (30) in the liquid container has fallen below the second NTC temperature sensor (12).

3. Fill-level measuring device according to claim 1, comprising an evaluation device (4) with a data storage device and a data processing device, which is configured to distinguish a second comparison value from a first comparison value by comparing the continuously measured comparison value with a reference value stored in the data storage device.

4. Fill-level measuring device according to claim 1, characterized in that the comparison value is a difference value, and in that the electronic measuring device (3) is configured to form a difference between the first electrical quantity of the first NTC temperature sensor (11) and the second electrical quantity of the second NTC temperature sensor (12), and to determine the comparison value by continuous difference formation of the first and second electrical quantities.

5. Fill-level measuring device according to claim 1, characterized in that the electronic measuring device (3) is configured such that the first and the second NTC temperature sensor are arranged in a bridge circuit (200) and that the bridge voltage of the bridge circuit (200) is used as the first and the second comparison value respectively.

6. Fill-level measuring device according to claim 5, characterized in that the electronic measuring device (3) comprises a voltage-controlled current source as electronic circuit (400) whose input voltage is the bridge voltage.

7. Fill-level measuring device according to claim 1, characterized in that the holding device (5) comprises a capsule device (14) made of a first material (M1) and in that at least one sensor contact surface (11a, 12a) of the first and/or the second NTC temperature sensor (11, 12) made of a second material M2) are provided, such that the capsule device (14) encloses the at least one sensor contact surface (11a, 12a) and the capsule device (14) and the at least one sensor contact surface (11a, 12a) outwardly delimit the first and/or the second NTC temperature sensor (11, 12).

8. Fill-level measuring device according to claim 7, characterized in that the second material (M2) has a higher thermal conductivity than the first material (M1).

9. Fill-level measuring device according to claim 8, characterized in that the first material (M1) is a plastic and the second material (M2) is a metal.

10. Fill-level measuring device according to claim 7, characterized in that the first NTC temperature sensor (11) and its sensor contact surface (11a) and/or the second NTC temperature sensor (12) and its sensor contact surface (12a) are each enclosed by a socket (11b, 12b), such that the capsule device (14), the socket (11b, 12b) of the first and/or the second NTC temperature sensor (11, 12) directly and the at least one sensor contact surface (11a, 12a) of the first and/or the second NTC temperature sensor (11, 12) indirectly limit the outside.

11. Fill-level measuring device according to claim 10, characterized in that the socket (11b, 12b) is made of a third material (M3).

12. Fill-level measuring device according to claim 1, characterized in that the holding means (5), the first NTC temperature sensor (11) and the second NTC temperature sensor (12) are made of materials capable of withstanding operating temperatures of the interior of the laboratory cabinet device of up to 180° C.

13. Laboratory cabinet device (100) for storing laboratory samples having a liquid container (31) in the interior (101) of the laboratory cabinet device (100) and a fill-level measuring device (1) according to claim 1 for measuring a fill-level (30) in the liquid container (31).

14. Fill-level measuring device according to claim 9, characterized in that the metal is a stainless steel.

15. Fill-level measuring device according to claim 11, characterized in that the third material (M3) is a polyether ether ketone (PEEK).

16. Laboratory cabinet device according to claim 13, which is a tempering cabinet.

* * * * *